United States Patent
Rathjen et al.

(10) Patent No.: US 9,849,037 B2
(45) Date of Patent: Dec. 26, 2017

(54) PATIENT INTERFACE FOR OPHTHALMOLOGICAL, OPTICAL THERAPY AND DIAGNOSIS DEVICE

(71) Applicant: Ziemer Ophthalmic Systems AG, Port (CH)

(72) Inventors: Christian Rathjen, Bremen (DE); Thomas Studer, Neuchatel (CH)

(73) Assignee: Ziemer Opthalmic Systems AG, Port (CH)

( * ) Notice: Subject to any disclaimer, the term of this patent is extended or adjusted under 35 U.S.C. 154(b) by 531 days.

(21) Appl. No.: 14/498,461

(22) Filed: Sep. 26, 2014

(65) Prior Publication Data

US 2015/0088103 A1  Mar. 26, 2015

(30) Foreign Application Priority Data

Sep. 26, 2013 (CH) ........................................ 1673/13

(51) Int. Cl.
*A61F 9/009* (2006.01)
(52) U.S. Cl.
CPC .................................. *A61F 9/009* (2013.01)
(58) Field of Classification Search
CPC ........................................................ A61F 9/009
USPC ................................................... 606/4, 5, 10
See application file for complete search history.

(56) References Cited

U.S. PATENT DOCUMENTS

| 8,556,425 | B2 * | 10/2013 | Frey | A61F 9/00825 |
| | | | | 351/208 |
| 8,632,526 | B2 * | 1/2014 | Brownell | A61F 9/00827 |
| | | | | 351/208 |
| 2002/0103481 | A1 * | 8/2002 | Webb | A61F 9/009 |
| | | | | 606/5 |

(Continued)

FOREIGN PATENT DOCUMENTS

| EP | 1 731 120 A1 | 12/2006 |
| WO | 2012031277 A1 | 3/2012 |

OTHER PUBLICATIONS

Dec. 11, 2014—(EP) Extended Search Report—App 14003135.2—no English translation provided.

*Primary Examiner* — Gary Jackson
*Assistant Examiner* — Zahed Kabir
(74) *Attorney, Agent, or Firm* — Banner & Witcoff, Ltd.

(57) ABSTRACT

A patient interface for coupling an ophthalmological application head to an eye of a patient includes a patient-sided interface structure to be coupled to the eye of a patient, and a source-sided interface structure for rigidly coupling the patient interface to the application head or an intermediate element. The source-sided interface structure comprises a first source-sided patient interface coupler and a second source-sided patient interface coupler. The first source-sided patient interface coupler is designed to restrict the mobility of the patient interface relative to the application head or the intermediate element by providing a coupling with a first patient interface coupler counterpiece of the application head or the intermediate element. The second source-sided (Continued)

patient interface coupler is designed to rigidly couple the patient interface to the application head or the intermediate element while the first source-sided patient interface coupler is coupled with the first patient interface coupler counterpiece.

16 Claims, 8 Drawing Sheets

(56) References Cited

U.S. PATENT DOCUMENTS

| | | | |
|---|---|---|---|
| 2007/0093795 A1* | 4/2007 | Melcher | A61F 9/009 606/10 |
| 2008/0071254 A1* | 3/2008 | Lummis | A61F 9/009 606/4 |
| 2008/0287927 A1 | 11/2008 | Rathjen | |
| 2011/0022035 A1* | 1/2011 | Porter | A61F 9/00825 606/4 |
| 2012/0283708 A1* | 11/2012 | Raksi | A61F 9/009 606/4 |
| 2013/0035674 A1 | 2/2013 | Lummis et al. | |
| 2013/0103014 A1* | 4/2013 | Gooding | A61B 3/102 606/6 |
| 2013/0226158 A1* | 8/2013 | Rathjen | A61F 9/00825 606/4 |
| 2013/0345682 A1* | 12/2013 | Hailmann | A61B 19/56 606/4 |

* cited by examiner

PATIENT INTERFACE FOR OPHTHALMOLOGICAL, OPTICAL THERAPY AND DIAGNOSIS DEVICE

CROSS REFERENCE TO RELATED APPLICATIONS

This application claims priority to Switzerland Application No. 01673/13, filed Sep. 26, 2013, the disclosure of which is incorporated herein by reference in its entirety.

TECHNICAL FIELD

The present invention relates to a patient interface for coupling an ophthalmological application head for application of optical radiation of a radiation source on an eye of a patient and an intermediate element to be arranged between a patient interface and the ophthalmological application head. The invention further relates to an ophthalmological application head designed for use in conjunction with a patient interface for the use of optical radiation of a radiation source. The invention further relates to a method for coupling the ophthalmological application head to an eye of a patient.

BACKGROUND

The use of lasers for the treatment and/or diagnosis of eye tissue is known. Such devices, for example, have a basic device with a laser light source for generating laser pulses, for example femtosecond laser pulses, and an application head with a projection objective which, for treatment, is coupled with the eye of the patient. The application head can be movably connected to the basic device, for example, by means of an articulated arm, wherein the articulated arm can simultaneously be used for the optical beam guidance from the laser light source to the application head. For example, such an arrangement is disclosed in EP 1 731 120. There are also devices with the application head integrated in the basic device or in which other device arrangements are provided.

The application head is mechanically and optically coupled to the eye of the patient, for example, to the cornea or the sclera of the eye of the patient, by means of a patient interface, wherein the patient interface can comprise a transparent contact body, with which the laser pulses emerging from the projection objective are guided and which, by means of mechanical contact with the cornea, secures said cornea with regard to the patient interface and the projection objective. Alternatively to coupling by means of a contact body, a liquid coupling can be provided, wherein a coupling liquid, for example, physiological salt solution, is located between cornea and projection objective. Corresponding patient interfaces, for example, are known from WO2012031277. The patient interface can be coupled to the eye of the patient by means of a vacuum and a suction ring placed on the cornea. Most suction rings have two sealing lips. The lips can be applied to the sclera, the sclera and the cornea, or only the cornea. Furthermore, there are variations which have only one ring and generate a vacuum across the entire eye, or variations consisting of a plurality of suction chambers/suction cups. The suction ring is the most common attachment method, however, there are also other known solutions. With the known systems, the patient interface is coupled to the application head, for example, by means of a screw connection, bayonet connectors, or vacuum couplings U.S. 2008/287927 describes a protective device for ophthalmic laser treatment using a protective foil for protecting the eye from direct contact with a reference body arranged between the application head and the eye. The protective device comprises a suction ring for attachment to the eye and is designed to receive the protective foil, for example, by means of an annular carrier frame. The suction ring is provided with coupling means for attachment to the application head. According to U.S. 2008/287927, the coupling means are designed as screw connection, bayonet connector, or snapping mechanism.

U.S. 2012/0283708 describes an ophthalmological patient interface which can be coupled to an application head of a laser system and has a contact lens to be disposed on the eye. U.S. 2012/0283708 describes a flexible connection element attached to the contact lens which allows for a rotational and/or transversal movement of the contact lens relative to the application head during docking. Without further description, the document cites a "flex-and-lock" mechanism for inhibiting further movement of the contact lens relative to the application head.

For patient interfaces used in ophthalmological laser applications, there are a number of challenges and marginal conditions which make the transfer of numerous constructions known from other areas of application appear to be impossible or impractical from a practical point of view. Significant limitations result from the existing proximity of the devices to the eye of the patient and particularly the direct physical contact of the patient interface with the eye of the patient. In addition to high safety requirements, it follows that the patient interface is at least designed to be easily manageable and securely attachable.

Even though the space conditions in the vicinity of the operating site on the eye of the patient are narrow and crowded, the eye of the patient should be accessible and visible to the user during treatment. Patient interface and the other components should thus interfere very little with accessibility and visibility.

Due to the significant medical risks in case of a misdirection of the laser beam which can result in unwanted impairment and even destruction of eye tissue, components which are arranged in the region of the beam path from the light projector to the eye of the patient must be positioned and aligned correctly and safely coupled or connected to one another.

SUMMARY

It is an aspect to provide an application head for ophthalmological use of optical radiation of a radiation source which meet all or part of at least certain of the initially described requirements of the coupling of a patient interface to an application head with regard to a simple and secure connection.

It is another aspect to include a patient interface for coupling an ophthalmological application head for application of optical radiation of a radiation source on an eye of a patient comprises: a patient-sided interface structure, designed so as to be coupled to the eye of a patient, and a source-sided interface structure which is designed to rigidly couple the patient interface to the application head or an intermediate element provided to be arranged between application head and patient interface.

In another aspect, the source-sided interface structure comprises a first source-sided patient interface coupler and an additional second source-sided patient interface coupler. The first source-sided patient interface coupler is designed to restrict the mobility of the patient interface relative to the application head or the intermediate element by providing a coupling with a first patient interface coupler counterpiece of the application head or the intermediate element. The second source-sided patient interface coupler is designed to rigidly couple the patient interface to the application head or the intermediate element while the first source-sided patient interface coupler is coupled with the first patient interface coupler counterpiece by providing a coupling with a second patient interface coupler counterpiece of the application head or the intermediate element. The first source-sided patient interface coupler is thus advantageous because it is designed such that the mobility of the patient interface relative to the application head or the intermediate element is restricted by providing a coupling with the first patient interface coupler counterpiece of the application head or the intermediate element before the second source-sided patient interface coupler is coupled with a second patient interface coupler counterpiece of the application head or the intermediate element, i.e. without requiring a coupling of the second source-sided patient interface coupler with the second patient interface coupler counterpiece of the application head or the intermediate element for restricting the mobility of the patient interface relative to the application head or the intermediate element.

The terms "source-sided" and "patient-sided" as related to an element indicate that, in operational alignment, the element is facing the application head or the eye of the patient, and in operational condition, is directly or indirectly connected to the application head or the eye of the patient.

Restriction of mobility indicates that the number of mechanical degrees of freedom for movement is reduced, but at least one degree of freedom is still available. A rigid coupling indicates the elimination of all degrees of freedom and the rigidly coupled elements substantially act as a common body.

In the mounted state of the patient interface, a rigid coupling with the application head or intermediate element, if applicable, allows for a correct alignment of the laser pulses onto a target point or target region in the eye of a patient.

The first and the second source-sided patient interface coupler are preferably arranged on sides or walls of the patient interface facing one another.

Therefore, the patient interface predetermines the following approach for mounting it to the application head or, if applicable, intermediate element: Proceeding from an initial uncoupled state in which the patient interface is not coupled with and thus separate from the application head or, if applicable, intermediate element, a first coupling is initially effected by coupling the first source-sided patient interface coupler with the first patient interface coupler counterpiece. While maintaining said first coupling (and only then), the patient interface can be moved relative to the application head or, if applicable, intermediate element by a movement, e.g. a tilting or swiveling movement, until an additional second coupling is effected by coupling the second source-sided patient interface coupler with the second patient interface coupler counterpiece.

Advantageously, the patient interface and the application head or, if applicable, intermediate element are designed such that the movement of the patient interface required for the second coupling is possible with one (single) hand.

The first and second source-sided patient interface coupler are designed for a detachable coupling, particularly a non-destructively detachable coupling, with the corresponding counterpieces. As described below, the couplers can be designed for simple detachment with few hand manipulations in a single-handed operation.

The single-handed application and detachment of the coupling of the patient interface with the application head or the intermediate element is particularly advantageous with the use of ophthalmological laser systems with the application head attached to a swivel arm and to be held or guided by hand. For the user, it is thus possible to hold the application head with one hand while using the other hand to carry out the coupling to and detachment from the patient interface and, if applicable, an intermediate element with a few simple movements of the hand.

Advantageously, the patient interface is designed as disposable product for a single use during eye treatment and subsequent disposal. The patient interface can be designed as multi-component injection-molded part made of plastic. Additionally or alternatively, further materials such as metal and/or further manufacturing techniques such as deep-drawing, or cutting processing, or 3D printing technique can be used.

The patient interface can be designed so as to be bowl-shaped and, toward the application head or the intermediate element, be substantially concave and, toward the patient, be substantially convex, wherein the concave shape can be complementary to a corresponding convex shape of the application head or intermediate element.

In one exemplary embodiment, the first source-sided patient interface coupler is designed to interlockingly couple with the first patient interface coupler counterpiece while maintaining at least one degree of freedom. It is interlockingly coupled by means of an approximately point-like coupling. The first source-sided patient interface coupler can be designed so as to be a notch, bore, blind hole, or generally a concave element, e.g. a depression in a wall of the patient interface. In this case, the corresponding first patient interface coupler counterpiece can be provided as convex element, for example, as a peg or nub on a wall of the application head or intermediate element. The arrangement is such that the convex element and the concave element, or the bore or notch, engage with one another, thus forming an interlocking connection when the patient interface is positioned on the application head or intermediate element. Alternatively or additionally, coupling, for example, can be achieved magnetically or by means of a vacuum. Furthermore, a convex element can be arranged on the patient interface and a corresponding concave element, a notch, or bore can be arranged on the application head or intermediate element. Depending on design, dimensions, and weight of the patient interface, the first source-sided patient interface coupler and the corresponding first counter coupler can each also be realized with a plurality of individual elements, for example, two or more pegs or nubs and a corresponding number of concave elements, bores, or notches. Advantageously, the individual elements are to be arranged such that, due to their design, they simultaneously form and/or release a coupling. As a result, all element pairs forming the first source-sided patient interface coupler and the corresponding first counter coupler are, at all times, each jointly either in a coupled or uncoupled state.

In one exemplary embodiment, the first source-sided patient interface coupler is designed to create a forced guide for the patient interface with regard to the application head or the intermediate element when coupled with the first patient interface coupler counterpiece. The forced guide can set the patient interface relative to the application head or the intermediate element such that for the patient interface, only one movement, for example, a tilting or swiveling movement, is possible in one direction which leads to a coupling of the second source-sided patient interface coupler with the second patient interface coupler counterpiece when the first source-sided patient interface coupler is already coupled with the first interface counter coupler. Such a forced guide can be realized in that, once the first source-sided patient interface coupler is coupled with the first interface counter coupler, inner walls of the concave shape of the patient interface bear, substantially free of play, against corresponding outer walls of the application head, thus forming a sliding guide for said inner walls.

In one exemplary embodiment, the coupling of the second source-sided patient interface coupler with the second patient interface coupler counterpiece requires that the first source-sided patient interface coupler is coupled with the first patient interface coupler counterpiece. Such a design ensures that a mounting of the patient interface is only possible in the designated and correct manner and the patient interface, in its mounted state, is correctly positioned and oriented relative to the application head or the intermediate element. Advantageously, the user only has to check the second interface coupler.

In one exemplary embodiment, the second source-sided patient interface coupler is designed to couple with the second patient interface coupler counterpiece by means of a snap or latch connection. As first source-sided patient interface coupler, the patient interface can have a spring latch and the first patient interface coupler counterpiece can have a corresponding counter latch. The spring latch and the counter latch can be arranged such that in an end position of the patient interface relative to the application head or intermediate element, they necessarily engage with one another, thus locking or catching the patient interface with the application head or intermediate element. The movement end position of the patient interface corresponds to the position and orientation of the patient interface relative to the application head or intermediate element in operational condition. In one exemplary arrangement, the second source-sided patient interface coupler comprises a snap lever, for example, a spring latch, releasable with one hand. It can be designed so as to be flexible and have on its end a latch for engaging with the counter latch. A one-handed release can be provided by means of an unlock key which is part of the snap lever and with which the mesh of latch and counter latch can be released by flexible bending of the latch, for example by means of pressure with finger or thumb. If the second source-sided patient interface coupler, for example for rigidity reasons, is realized through a combination of a plurality of individual snap levers, they can be structurally connected to allow a joint release of the snap or latch mesh with the counter latch and thus a release of the coupling.

In an alternative embodiment, the arrangement of spring latch and counter latch can be reversed. In further embodiments, an arrangement of convex elements on the patient interface, for example, nubs, and corresponding concave elements, notches, or bores on the application head or intermediate element, or vice versa, are used instead of interacting latches.

Insofar, snap or latch connections are particularly favorable because the completed coupling, i.e. the engaging or catching due to the occurring power discontinuity, is tactilely easily detectable and furthermore connected to a characteristic snapping or clicking sound, providing additional acoustic feedback to the user.

In principle, the second source-sided patient interface coupler and the corresponding second counter coupler can also be realized by two or more pairs of constructive single elements. The number of single elements for the first and second source-sided patient interface coupler can be identical or different. For example, embodiments are possible with the first source-sided patient interface coupler being formed by two bores which mesh for coupling with two corresponding pegs as first counter coupler while the second source-sided patient interface coupler is formed by a single spring latch which is symmetrically arranged to the bores.

In one exemplary embodiment, the patient interface is, at least to some extent, elastic. When forming the coupling of the second source-sided patient interface coupler with the second patient interface coupler counterpiece, the patient interface is elastically tensioned. Elastic tensioning of the patient interface ensures that the patient interface is attached tightly and free of play on the application head or the intermediate element while ensuring the correct position and orientation. An at least partial elasticity of the patient interface can be achieved through suitable shaping of the patient interface and the material selection, for example, using injection molding to produce said patient interface. With such a design, the patient interface overall has the required elasticity. Alternatively, specific elastic elements, e.g. springs, can also be used. Furthermore, elasticity can be realized through the first and/or the second source-sided patient interface coupler, in which case they are designed such that they are pre-tensioned in the coupled state, i.e., when meshing with the corresponding counter coupler.

In one exemplary embodiment, the coupling of the first source-sided patient interface coupler with the first patient interface coupler counterpiece requires that the second source-sided patient interface coupler is not coupled with the second patient interface coupler counterpiece. Such a design appropriately ensures that—in accordance with the specified mounting sequence for correct placement of the patient interface—the first source-sided patient interface coupler is always coupled first with its corresponding counterpiece and the second source-sided patient interface coupler is only subsequently coupled. This objective can be achieved through suitable arrangement of the first and second source-sided patient interface coupler and suitable design of said couplers as will be described in the following execution embodiments.

In one exemplary embodiment, the patient interface comprises a grip structure able to be held with one hand. In one possible design, said grip structure is integral with the second source-sided patient interface coupler. A grip structure able to be held by hand is favorable for fine positioning and alignment of the patient interface prior to or during the coupling with the application head or the intermediate element. A grip structure appears to be particularly advantageous when—in accordance with a possible application of the patient interface—the patient interface is first coupled to the eye of a patient and subsequently connected to the application head. For integration in the second source-sided patient interface coupler, an elastic snap lever, for example, as described above, an unlock key of a snap lever, can be designed as grip structure.

In one exemplary embodiment, the patient-sided interface structure comprises a suction ring for providing a rigid vacuum coupling with the eye of a patient. The suction ring is intended to be placed on the cornea of the eye of the patient and can have a double-wall structure with an inner wall and an outer wall coaxial and equidistant to the inner wall, wherein the space between the inner wall and the outer wall is designed as a annular hollow chamber for generating negative pressure or a vacuum and which is open toward the eye of a patient. The suction ring can have a connection which is fluidically coupled with the gap, for example, a connecting piece for connecting with a negative-pressure or vacuum pump. In such an arrangement, the laser beam, during application, runs through the space surrounded by the inner wall.

In one exemplary embodiment, the patient interface is designed to be filled, to some extent, with an optical coupling liquid, for example, physiological salt solution. The amount of coupling liquid to be filled is measured such that, after coupling the patient interface to the application head or intermediate element, a space between the patient interface and the application head or intermediate element is completely filled with liquid. The coupling liquid is preferably filled in after coupling the patient interface to the eye of a patient and prior to coupling the patient interface to the application head or intermediate element. Instead of a filling with liquid, the application head can also be coupled to the eye of a patient by means of a contact body placed on the eye of a patient. The contact body can be part of the application head or the patient interface. In addition, membranes and foils can be inserted as sterile barrier.

According to a further aspect, an intermediate element to be arranged between a patient interface and an ophthalmological application head is provided for application of optical radiation of a radiation source.

The intermediate element is provided to be arranged between an ophthalmological application head for application of optical radiation of a radiation source and a patient interface according to the disclosure and comprises: a patient-sided intermediate element interface structure, and a source-sided intermediate element interface structure.

The patient-sided intermediate element interface structure comprises a first patient-sided intermediate element coupler and an additional second patient-sided intermediate element coupler. The first patient-sided intermediate element coupler forms a first patient interface coupler counterpiece, and the second patient-sided intermediate element coupler forms a second patient interface coupler counterpiece.

The first patient-sided intermediate element coupler is designed to restrict the mobility of the patient interface relative to the intermediate element by coupling with the first source-sided patient interface coupler of the patient interface. The second patient-sided intermediate element coupler is designed to rigidly couple the patient interface to the intermediate element by coupling with the second source-sided patient interface coupler of the patient interface while the first patient-sided intermediate element coupler is already coupled with the first source-sided patient interface coupler.

The intermediate element is provided to be arranged between patient interface and application head, resulting in a sandwich structure in the mounted state. The intermediate element—similar to the patient interface—can be designed so as to be bowl-shaped. Toward the application head, it has a substantially concave shape which is complementary to a substantially convex shape of the application head. Toward the patient interface, such an intermediate element has a substantially convex shape which is complementary to a substantially concave shape of the patient interface. In such an arrangement, the intermediate element, similar to a protective cover, covers or encases a part of the application head facing the patient.

The first and second patient-sided intermediate element coupler are designed to interact with the first and second source-sided patient interface coupler of the patient interface. For example, if the first source-sided patient interface coupler is designed as concave element, e.g. a pin, peg or nubs, the first patient-sided patient interface coupler is correspondingly designed as convex element, for example in the form of a depression, bore, or notch, and vice versa. The same applies to the second patient-sided intermediate element coupler.

An intermediate element according to the disclosure can have an optically transparent separating body, for example, in the form of a transparent foil which, in a mounted state, bears against the exit window or projection objective of the application head.

The optional intermediate element separates the application head from the patient interface and protects the application head, e.g. from contamination. If, according to the above description, an optical coupling liquid is used, the optionally available transparent separating body, e.g. a foil or membrane, further protects the application head from contact with contact liquid which is possibly also contaminated with germs and tissue cells. Alternatively, the intermediate element can also contain a contact body.

In one exemplary embodiment, the source-sided intermediate element interface structure is designed to rigidly couple the intermediate element to the application head. The source-sided intermediate element interface structure comprises a first source-sided intermediate element coupler and a second source-sided intermediate element coupler. The first source-sided intermediate element coupler is designed to restrict the mobility of the intermediate element relative to the application head when coupled with a first application head coupler of the application head. The second source-sided intermediate element coupler is designed to rigidly couple the intermediate element to the application head by coupling with a second application head coupler of the application head while the first source-sided intermediate element coupler is already coupled with the first application head coupler.

In such a design of the intermediate element, the intermediate element is basically coupled to the application head the same way that the patient interface is coupled to the intermediate element. As a result, the fundamentally identical constructions and principles can be used for the design of the first and second source-sided intermediate element coupler. Therefore, for embodiments used as examples, reference is made to the above descriptions, wherein, with regard to the coupling with the application head, the intermediate takes the place of the patient interface.

In an exemplary but not mandatory operating method the isolated patient interface is coupled to the eye of a patient, for example, as described above, by means of a vacuum. Subsequently, the concave side of the patient interface, which is facing the application head during operating conditions, is, to some extent, filled with coupling liquid similar to a bowl, wherein the coupling liquid comes in direct contact with the cornea of the eye of a patient. Separately, the intermediate element is coupled to or mounted on the application head. In a last step, the patient interface coupled with the eye of a patient is coupled with the intermediate element.

The first and/or second source-sided intermediate element coupler and the corresponding counterpieces of the application head can each be formed, as described above, by a single element or by two/or more single elements, wherein the same deliberations and principles apply to number and arrangement.

According to a further aspect, an ophthalmological application head designed for use in conjunction with the patient interface is provided for the use of optical radiation of a radiation source.

The ophthalmological application head comprises a first application head coupler and a second application head coupler. The first application head coupler and the second application head coupler are designed as first patient interface coupler counterpiece for coupling with a first source-sided patient interface coupler and as second patient interface coupler counterpiece for coupling with an additional second source-sided patient interface coupler of the patient interface. Alternatively, the first application head coupler and the second application head coupler are designed for coupling with a first source-sided intermediate element coupler and a second source-sided intermediate element coupler of an intermediate element. The first and second application head coupler can be designed in exemplary embodiments as described above in conjunction with the coupling of the patient interface or intermediate element to the application head.

According to a further aspect, a method for coupling an ophthalmological application head for application of optical radiation of a radiation source on an eye of a patient is also provided.

The method for coupling the ophthalmological application head to an eye of a patient by means of a patient interface comprises the following sequential steps: establishing contact of the patient interface with the application head or an intermediate element provided so as to be arranged between application head and patient interface; restricting the mobility of the patient interface relative to the application head or the intermediate element by establishing a first coupling between the patient interface and application head or intermediate element; and rigid coupling of the patient interface to the application head or the intermediate element by establishing a second coupling between patient interface and application head while maintaining the first coupling.

The method can further comprise the step of a rigid coupling of an intermediate element to the application head. Further optional method steps follow directly from the above description of patient interface, intermediate element, and application head as well as the following embodiments.

In particular, the patient interface and the intermediate element form an ophthalmological protection system for use with the application head which is suitable for executing the described method. Therefore, disclosed embodiments of patient interface, intermediate element, and application head at the same time disclose corresponding embodiments of a corresponding protection system and method. Similarly, method steps described by way of example at the same time disclose corresponding embodiments of patient interface, intermediate element, and application head, and of a protection system thus formed.

BRIEF DESCRIPTION OF THE DRAWINGS

In the following, an embodiment of the present invention is described using an example. The example of the embodiment is illustrated by the following attached drawings.

DETAILED DESCRIPTION

Figure 1:
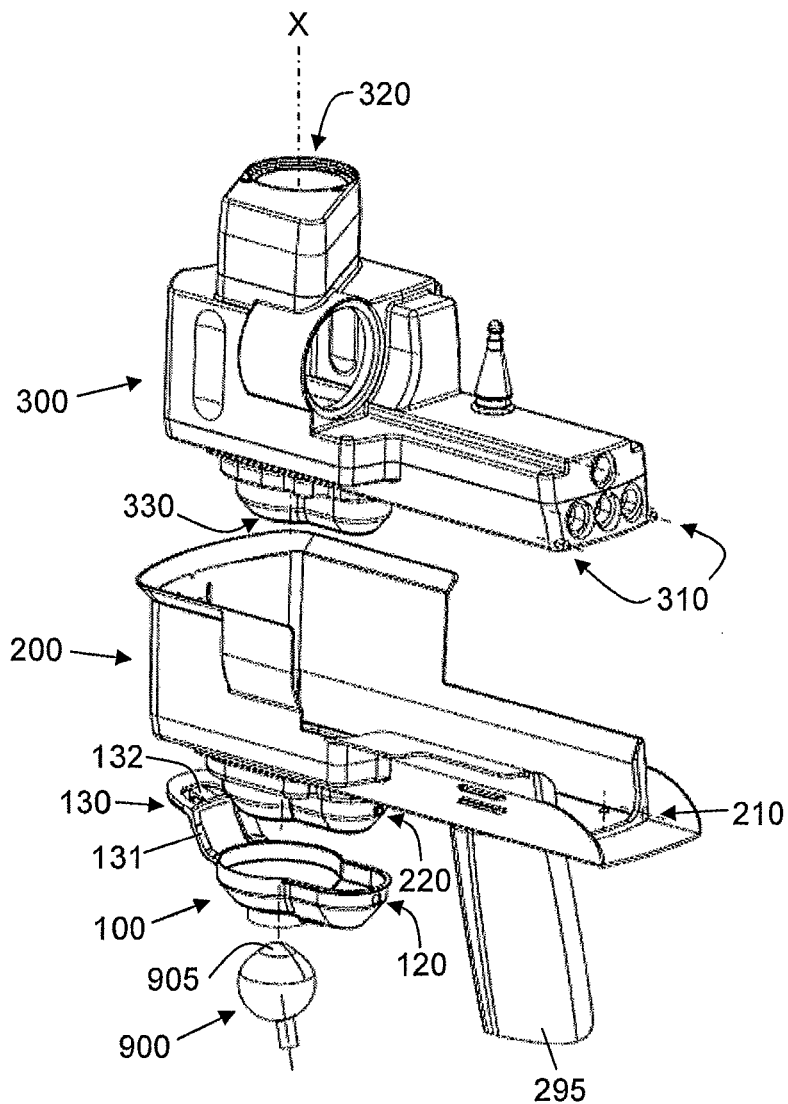
FIGS. 1 and 2 show an application head for application of optical radiation of a radiation source together with an intermediate element, a patient interface, and an eye of a patient.

FIG. 1 shows an application head 300 for application of optical radiation of a radiation source, an intermediate element 200 and a patient interface 100 in isometric view. The radiation source is particularly a laser source for generating laser pulses or a pulsed laser beam, for example, for generating femtosecond laser pulses. In the following, the description, by way of example, emphasizes laser pulses, but it will be clear to a person skilled in the art that other optical radiation and radiation sources can be used. The application head can be used for therapeutic but also diagnostic purposes. It is also conceivable that not only one application head is coupled to the patient interface 100, as described in the following, but a plurality of application heads, e.g. one for surgical and another for diagnostic purposes. It is also possible that initially one laser is used for therapy, that said laser is subsequently removed but the patient interface 100 remains docked. Then, a different surgical procedure, such as removal of the interior of the lens of the eye 900, is performed and the application head eventually reapplied, for example, to perform a posterior capsulotomy of the capsular bag remaining in the eye.

Figure 2:
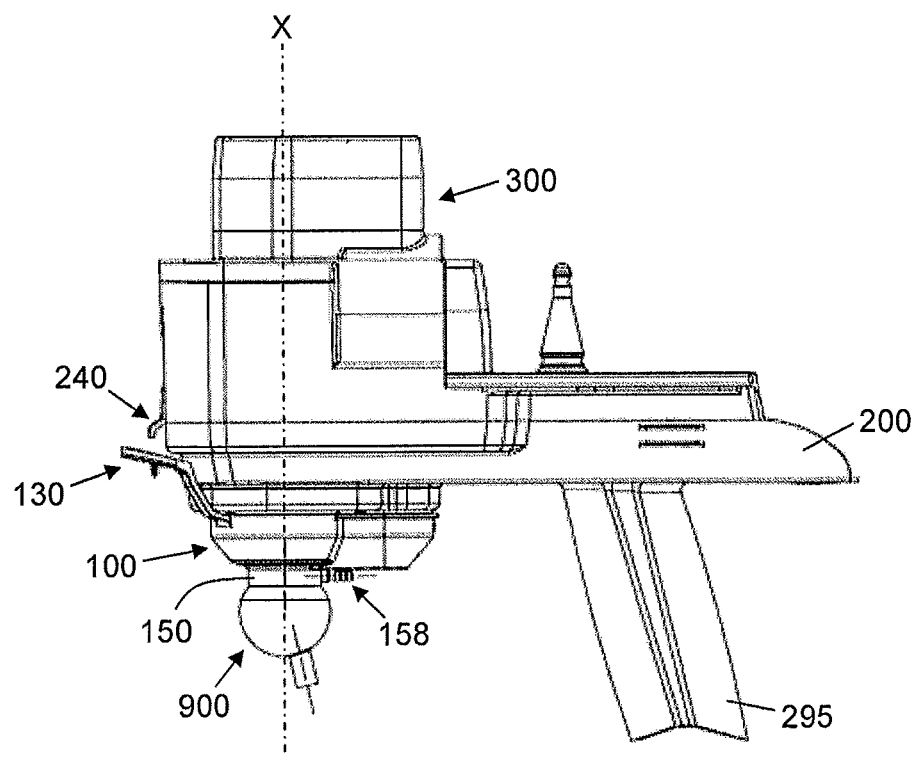

FIG. 2 shows a side view of the same elements in the coupled or mounted application state. For clarification, the elements are depicted together with an eye of a patient 900 with cornea 905. In FIG. 1, the relative position of patient interface 100, intermediate element 200, and application head 300 corresponds to that of FIG. 2, however, the elements are separated by an offset along the optical projection axis X.

The application head 300 (for application of optical radiation of a radiation source) has a housing with a substantially convex shape. On a front side, the first application head coupler protrudes from the application head; said application head coupler being formed, for example, by two pins 310 as shown in FIGS. 1 and 4a to 4e.

The intermediate element 200 has a bowl-like shape and, in the side facing the application head 300, has a substantially concave shape, corresponding to the shape of the housing of the application head 300. In the mounted state, the intermediate element 200, similar to an envelope, is put over a part of the application head 300, which faces the patient, or its housing and encompasses the application head 300 free of play. By way of example, the intermediate element 200 also has a handle 295 which, in the mounted state, points away from the application head 300, as shown in FIGS. 1 and 2. Furthermore, the intermediate element 200 has a laser passage window 260. In one variation of the embodiment, the laser passage window 260 is covered with a transparent and flexible protective foil which, for example, is attached on a movable carrier which, in turn, is attached continuously to the edge of the laser passage window 260.

The first source-sided intermediate element coupler which corresponds to the pins 310 of the first application head coupler is, by way of example, realized by two bores 210, only one of which is shown in FIGS. 1 and 4a to 4e. The second source-sided intermediate element coupler which, relative to the first source-sided intermediate element coupler, is arranged on the opposite front side of the intermediate element 200 is designed as spring latch 240. When coupled with the application head 300, it engages with a recess 340 (not visible in FIG. 1, FIG. 2) of the housing of the application head 300. Correspondingly, the recess 340 is the second application head coupler.

Similar to the intermediate element 200, the patient interface 100 also has a bowl-like shape. The side facing the application head 300 and the intermediate element 200 has a substantially concave shape, corresponding to the convex shape of the intermediate housing 200 facing the patient. In the mounted state, the patient interface 100, similar to an envelope, is put over a part of the intermediate element 200 which faces the patient and rigidly coupled with said intermediate element 200.

The patient interface 100 comprises a suction ring 150 with a circular profile, the outer diameter of which is measured such that it can be placed entirely on the sclera. A sucking nozzle 158 protrudes from one side of the suction ring 150 to be connected to a (not depicted) vacuum pump.

The first source-sided patient interface coupler of the patient interface 100 is formed, by way of example, by a bore 120 in a wall of the patient interface 100, as shown in FIGS. 1, 3a, 3b, and 4b to 4e. The bore 120 corresponds to a peg 220 protruding from the intermediate element 200 which represents the first patient-sided intermediate element coupler and is illustrated in FIGS. 1 and 4a to 4c.

By way of example, the second source-sided patient interface coupler of the patient interface 100 is formed by a spring latch 130. The corresponding second patient-sided intermediate element coupler is formed by a counter latch 230, corresponding to the latch 130, as protrusion on the intermediate element 200, as shown in FIGS. 4a to 4e and 5.

At this point, it must be noted that the observation window 320 shown in FIG. 1 allows a user a view onto the eye of a patient 900 in the state of the system docked to the eye of a patient 900, consisting of patient interface 100, if applicable, intermediate element 200, and application head 300. A view onto the cornea 905 of the eye of a patient 900 is made available through the application head 300, the laser exit window 330, the laser passage window 260 (including protective foil, if applicable) of the intermediate element 200, and the suction ring interior 154 of the patient interface 100.

Figure 3A:
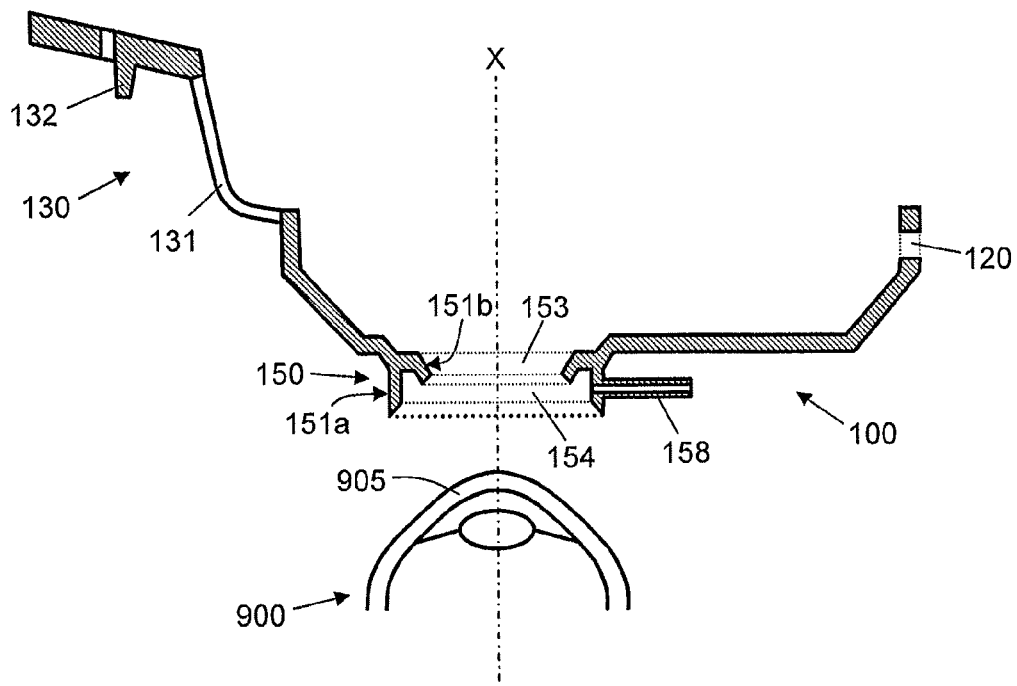
FIGS. 3a and 3b schematically show a cross-section of a patient interface together with an eye of a patient
Figure 3B:
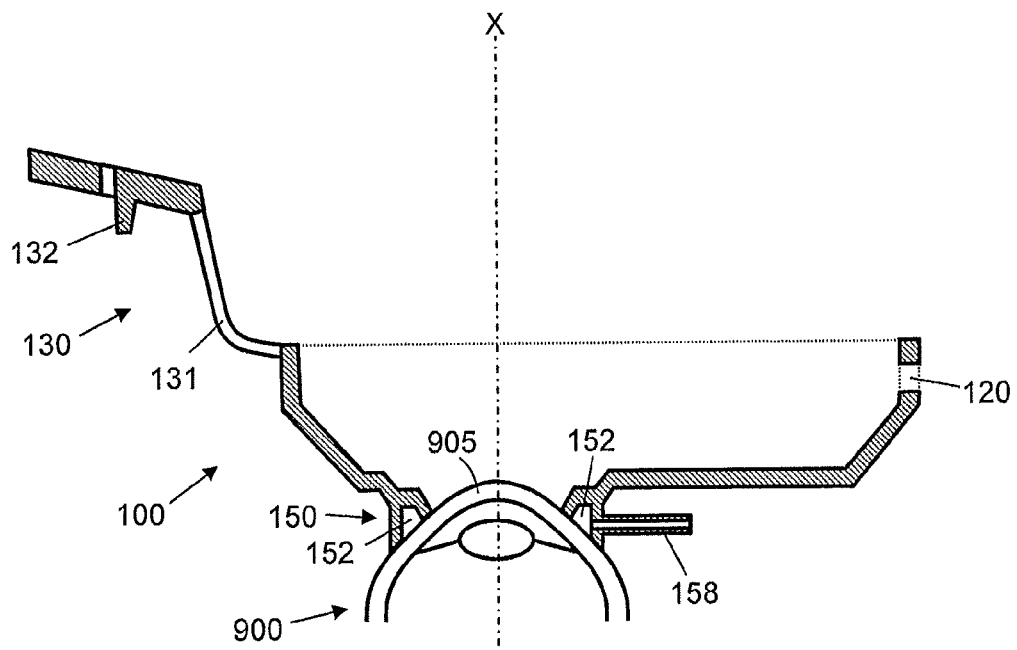

In the following, specific reference is made to FIGS. 3a, 3b. FIG. 3a shows the patient interface 100 schematically in a cross-section drawing together with an implied eye of a patient 900 in a disassociated state; FIG. 3b shows patient interface 100 and eye 900 in the coupled state.

In coaxial arrangement, the suction ring 150 comprises a suction ring inner wall 151b and a suction ring outer wall 151a, the shapes of which are adjusted to the curvature of the eye 900. As can be seen particularly in FIG. 3b, suction ring outer wall 151a and suction ring inner wall 151b together form an annular hollow chamber 152, the end faces of which bear against the cornea 905 with the sucking nozzle opening into said hollow chamber 152. In the state shown in FIG. 3b, the hollow chamber 152 can be evacuated by means of the sucking nozzle 158 and set under negative pressure, thus rigidly coupling the patient interface 100 to the eye 900. As a result, the eye of a patient 900, particularly a part of the cornea 905, protrudes into the suction ring interior 154 which is delimited by the suction ring inner wall 151b.

The first source-sided patient interface coupler 130 comprises two spring arms 131 and an unlock key 132 which is designed so as to have a grip structure graspable by hand (see also FIG. 1).

Figure 4A:
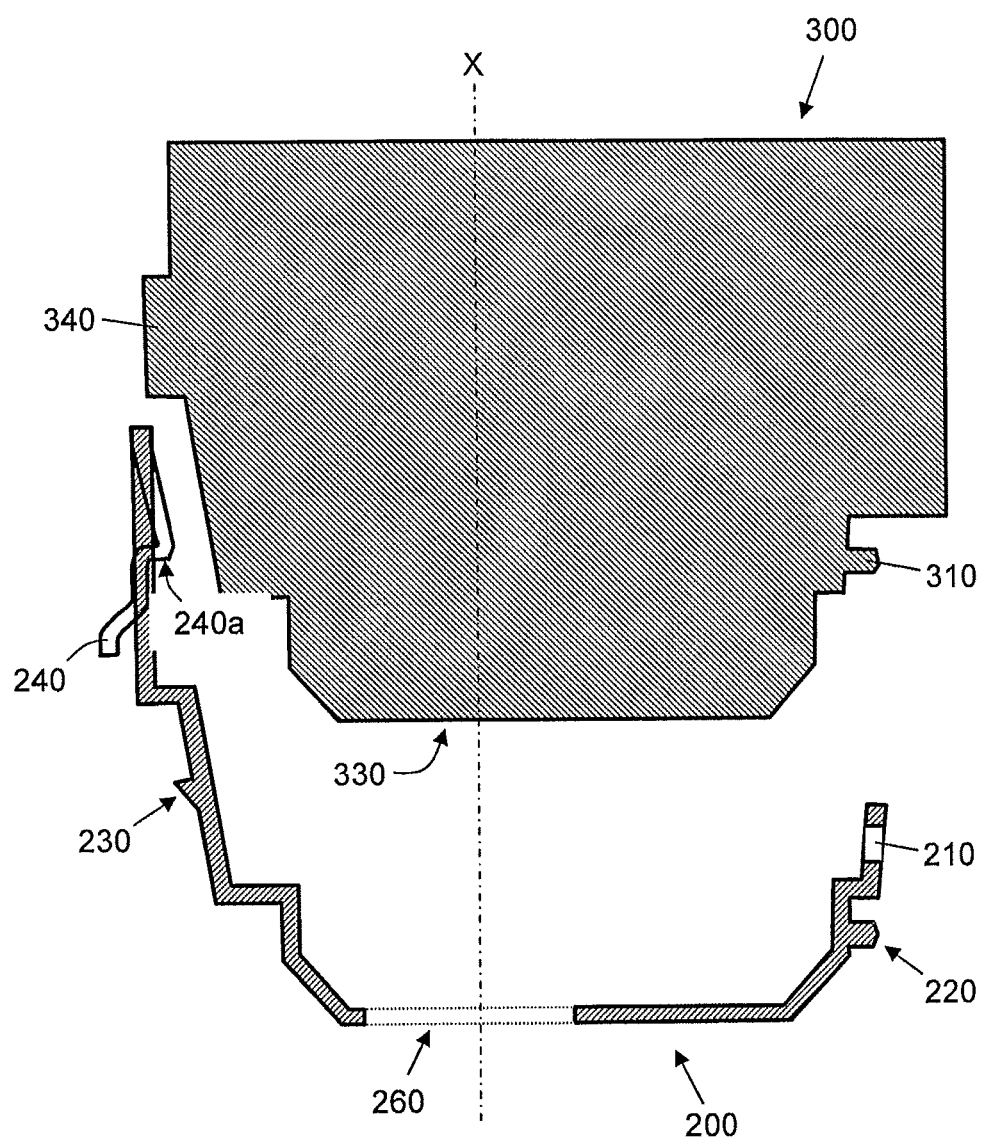
FIGS. 4a, 4b, 4c, 4d, 4e illustrate with schematic cross-sectional views the coupling of a patient interface, an intermediate element, and an application head.
Figure 4B:
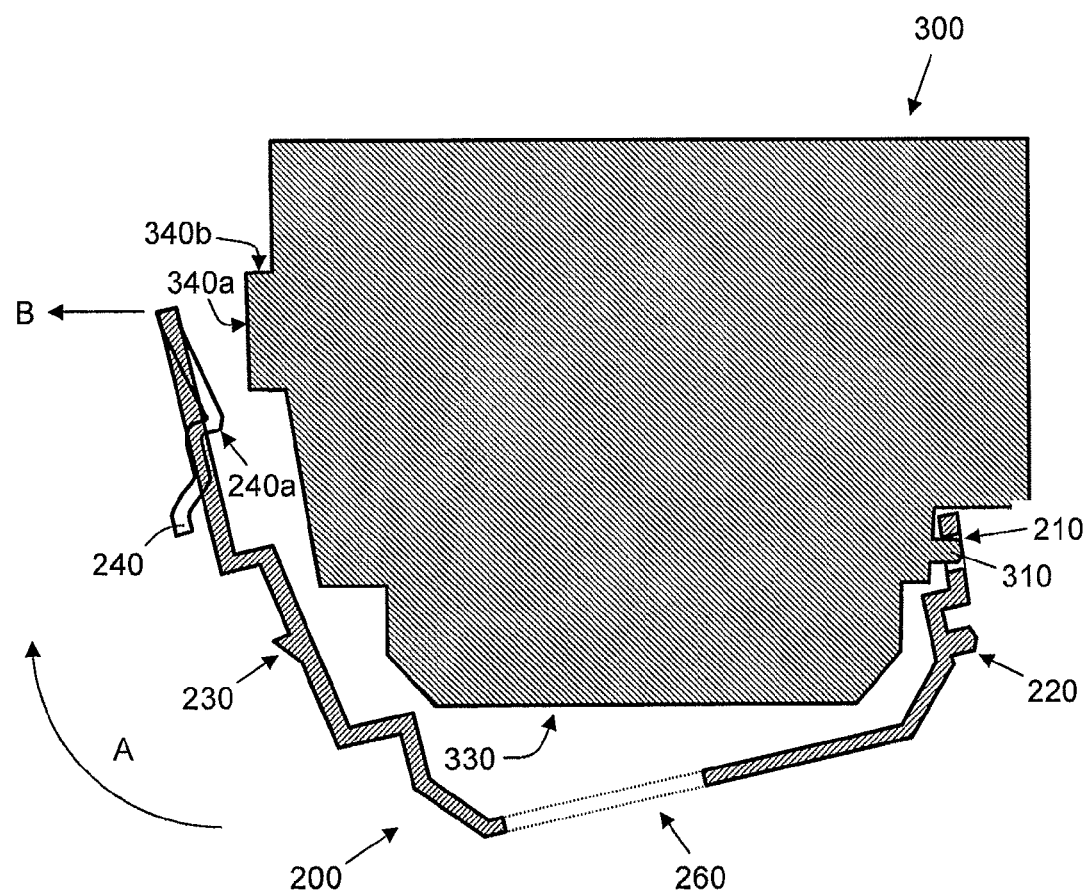
Figure 4C:
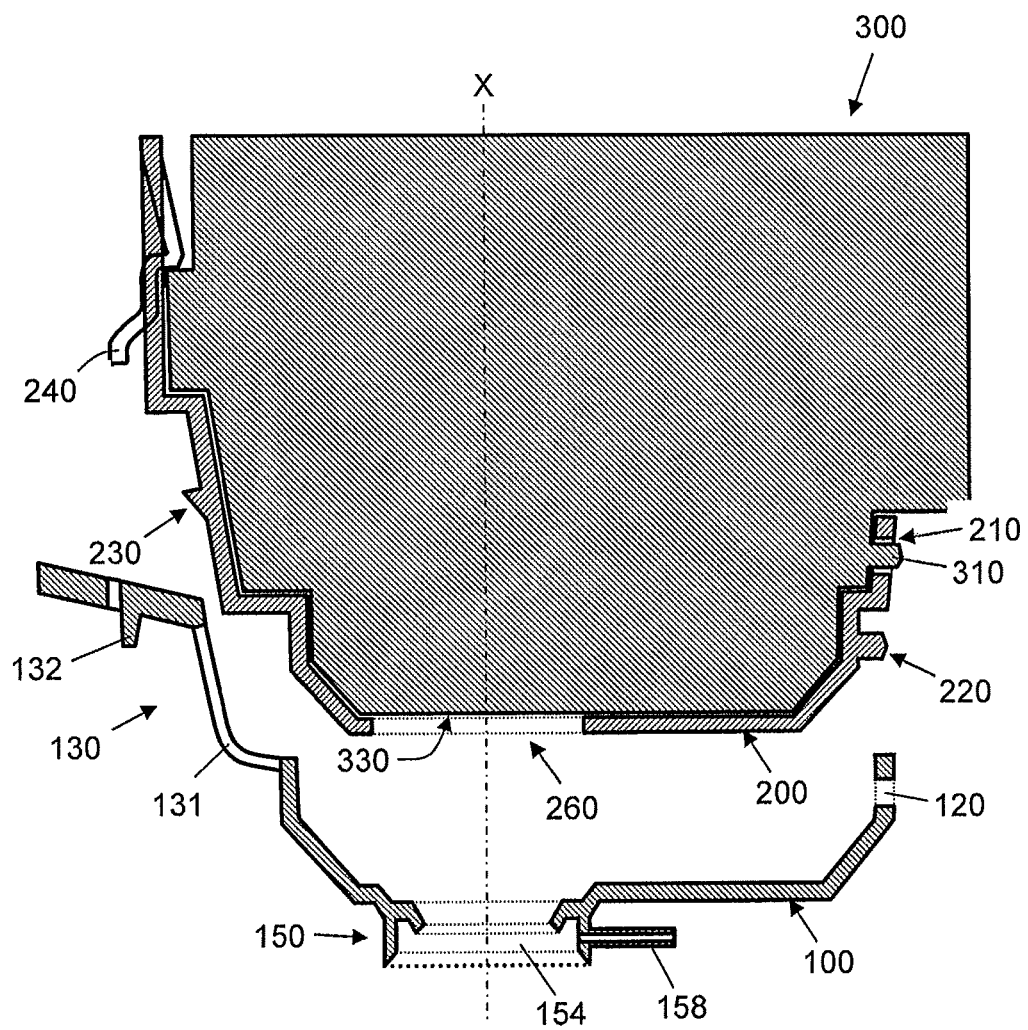

In the following, explicit reference is made to FIGS. 4a, 4b, 4c, 4d, and 4e. FIGS. 4a, 4b, and 4c illustrate in a schematic depiction the coupling or mounting of the initially separate (see FIG. 4a) intermediate element 200 to the application head 300. For mounting, the first application head coupler (pin 310) is at first coupled with the first source-sided intermediate element coupler (bore 210), thus restricting the mobility of the intermediate element 200 relative to the application head 300. In the depicted embodiment, this is effected in that the pins 310 (first application head coupler) are mounted in the bores 210 (first source-sided intermediate element coupler). In this state, as depicted in FIG. 4b, the intermediate element 200 is inclined or tilted relative to the application head 300.

Subsequently, the intermediate element 200 is tilted or swiveled relative to the application head 300 in the direction indicated by arrow A (see FIG. 4b), wherein the coupling formed by engaging the pins 310 in the bores 210 remains in place. In the course of this movement, the edge 240a of the spring lever 240 comes in contact with the interaction surface 340a of the recess 340. Continuing the tilting or swiveling movement in direction A causes the spring lever 240 to be deflected outward, i.e. away from the application head 300 and, during this movement, slides over the interaction surface 340a. Once the edge 240a slides over the interaction surface 340a and the catch surface 340b of the recess 340, the force exerted by the interaction surface 340a in direction B ceases to act and the spring lever 240 snaps back in reverse direction B in the direction of application head 300 to an end position, in which the spring lever 240 rests on the catch surface 340b. This corresponds to the end position of the intermediate element 200, in which the intermediate element 200 is rigidly coupled or mounted to the application head 300. This configuration is depicted in FIG. 4c. Solutions are also possible which are based solely on translation.

Figure 5:
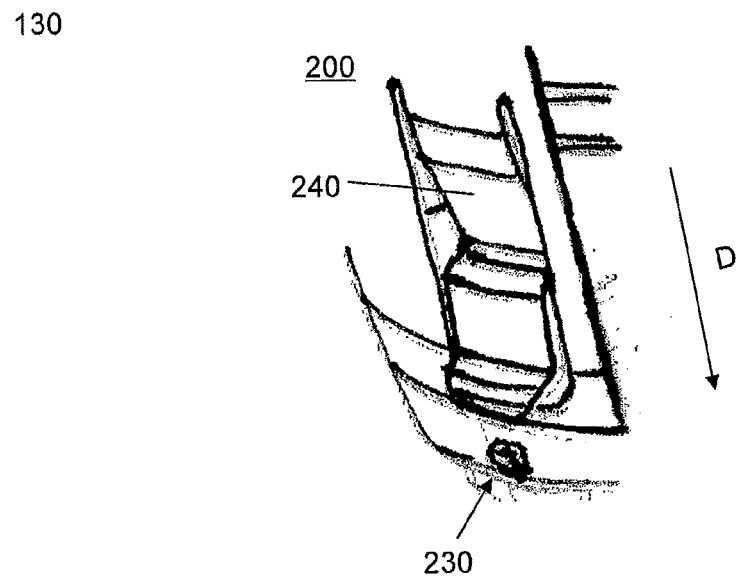
FIG. 5 shows a section of an intermediate element.

In a schematic isometric depiction, FIG. 5 shows the exterior view of a section of the intermediate element 200 with spring latch 240.

The intermediate element 200 can be subsequently separated from the application head 300 by simply pulling the spring latch 240 outward, i.e. away from the application head 300 in direction B, wherein the mesh of spring latch 240 and catch surface 340b is released.

Advantageously, spring latch 240 and recess 340 are designed such that the spring latch 240 in the end position according to FIG. 4c is not entirely relaxed but applies spring force inward (in reverse direction B) to the application head 300, ensuring a defined seating free of play of the intermediate element 200 on the application head 300. Furthermore, in the mounted state of FIG. 3, the entire intermediate element 200 can be slightly elastically stretched. In addition, the outer contour of the application head 300 and the inner contour of the concave shape of the intermediate element 200 form a sliding pairing substantially free of play. The housing of the application head 300 thus bears substantially free of play against the inner wall of the intermediate element 200. Due to the preferably present elasticity of the intermediate element 200, the housing of the application head 300 can, in the relaxed initial state, also have a slight excess over the inner contour of the intermediate element 200.

Figure 4D:
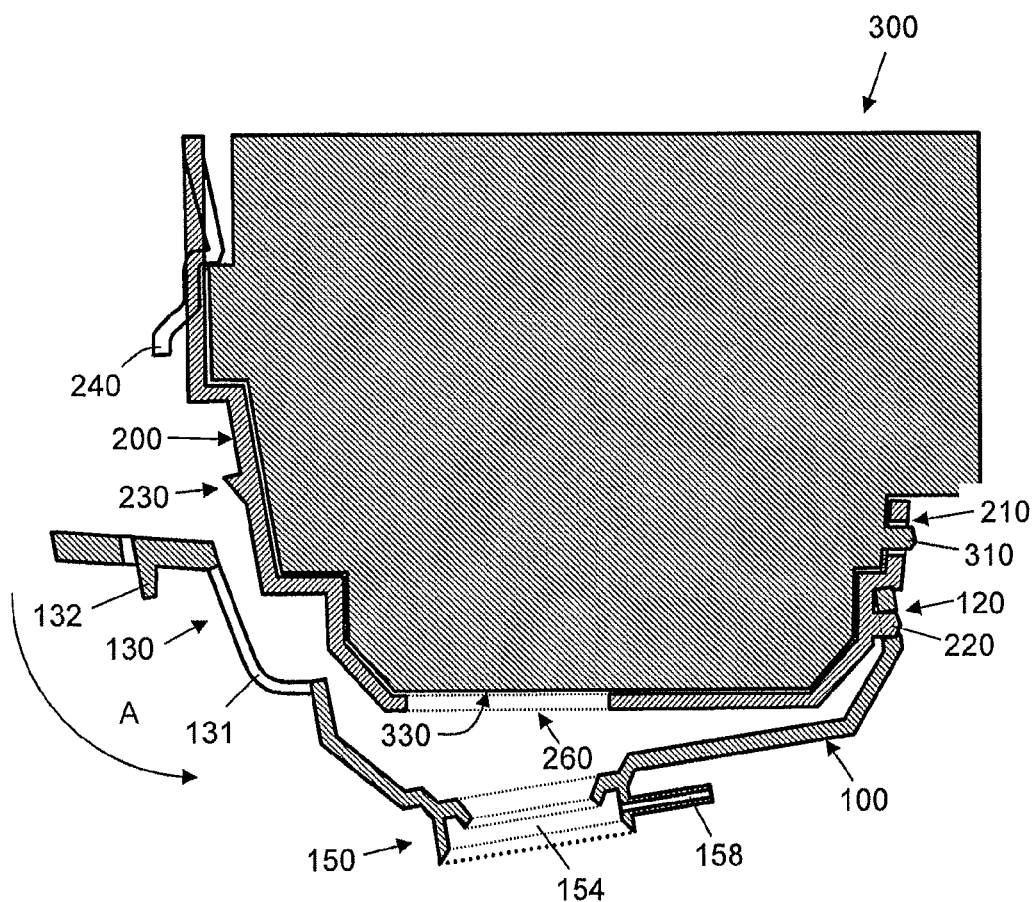
Figure 4E:
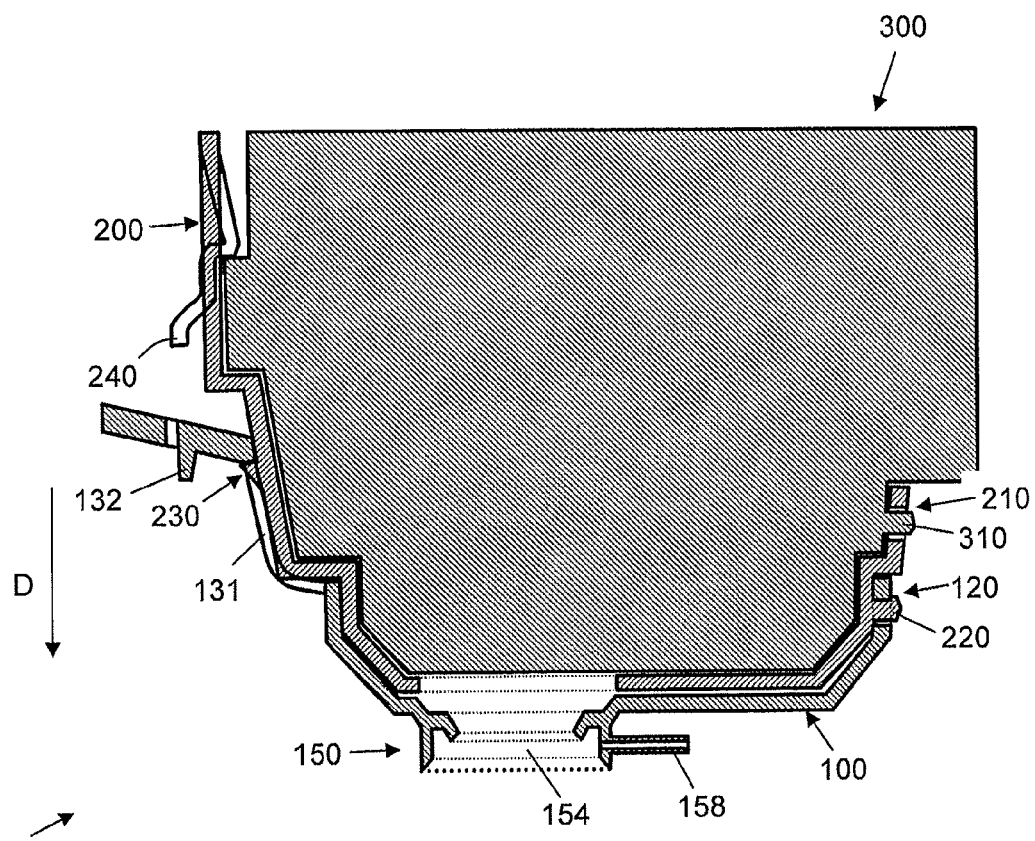

FIGS. 4c, 4d, 4e further show the assembly or coupling of the patient interface 100 to the intermediate element 200 or the application head 300. FIG. 4c shows the patient interface in a position disassociated from intermediate element 200 and application head 300. Even though it is not depicted for reasons of clarity and comprehensibility, the patient interface 100 can already be coupled to the eye of a patient 900 by means of the suction ring 150, as described above with reference to FIGS. 3a, 3b. Alternatively, the patient interface 100 can also be mounted in isolation.

The patient interface 100 is mounted to the intermediate element 200 in basically the same manner as the mounting of the intermediate element 200 to the application head 300 and is thus described correspondingly briefly.

For mounting, at first the source-sided patient interface coupler (bore 120) is coupled with the first patient-sided intermediate element coupler (pin 220) and the mobility of the patient interface 100 relative to the intermediate element 200 and application head 300 thus restricted. Similar to the first application head coupler 310, the first patient-sided intermediate element coupler 220 is designed so as to be a pin 220; similar to the first source-sided intermediate element coupler 210, the first source-sided patient interface coupler is designed so as to be a bore 120. Due to the smaller dimensions of the patient interface 100, as compared to the intermediate element 200, a single pin 220 and a single bore 120 are provided, e.g. centrally arranged, by way of example. The state after mounting the pin 220 (first patient-sided intermediate element coupler) in bore 120 (first source-sided patient interface coupler) is shown in FIG. 4d.

Particularly, if the patient interface 100 is already coupled to the eye of a patient 900 and the interior of the patient interface 100, if applicable, is to some extent filled with coupling liquid (if applicable, liquid is injected after the patient interface 100 is coupled to the eye 900 and coupled to the application head), the required relative movement is performed, as preferred in practice, primarily not by moving the patient interface 100 but by moving the application head 300 with intermediate element 200, wherein the patient interface 100 is, e.g., supported and held by means of its grip structure. In other words, in practice, deviating from the schematic depiction in FIG. 4d, the application head 300 with the attached intermediate 200 is tilted and mounted on the patient interface 100 by mounting the pin 220 in the bore 120 without having to move the patient interface 100 or the eye 900 while the patient interface 100 is already attached to the eye 900.

In an embodiment variation, the patient interface 100 has a patient interface interior 153 (see FIG. 3a) which conically tapers toward the eye of a patient 900, for example, such that the interior 153 defined by the inner suction ring wall 151b increasingly narrows in the applied state in the direction of the eye of a patient 900. The patient interface interior 153 is provided for (removably) receiving a correspondingly conically designed transparent contact body (instead of the liquid). On the side of the source, the contact body has a plane surface toward the application head 300 or its laser exit window 330 (e.g. running normally to the optical axis). On the side of the source, the contact body can be coupled to the application head 300 (e.g. to a plane laser exit window). In a variation, the contact body is designed so as to be flat on the (tapered) side facing the eye 900 and thus leveling the eye 900 or the cornea 905 in the applied state. Different patient interfaces 100 can also be provided, one for leveling with a contact body, the other for receiving liquid. Materials used for the contact body can be rigid, elastic, or gelatinous materials.

Subsequently, the patient interface 100 is tilted or swiveled relative to the application head 300 and the intermediate element 200 in the direction indicated by arrow A, wherein the mesh between pin 220 and bores 120 remains intact. Similar to the previous movement, the patient interface 100 can be held and the application head 300 with the intermediate element 200 can be tilted or swiveled instead.

In the end position, the spring latch 130 as second source-sided patient interface coupler engages with the counter latch 230 (see also FIG. 5) as second patient-sided intermediate element coupler, as shown in FIG. 4e. The counter latch 230 acts together with the spring latch 130 in the same manner as the spring latch 240 with the recess 340, wherein it is apparent that each of the specific designs used here is nonessential for the function and thus merely represent embodiments.

The patient interface 100 can subsequently be separated from the intermediate element 200 by simply pressing the unlock key 132 in direction C, i.e. away from the application head 300. This releases the mesh of spring latch 130 and counter latch 230.

Since the intermediate element 200 is mounted or coupled to the application head 300 and the patient interface 100 is mounted or coupled to the intermediate element 200 in an analog manner and according to the same principles, it is further apparent that with a corresponding constructive design of patient interface 100 and application head 300, a direct coupling of these elements is also possible in the same manner without the intermediate element 200.

In one variation, the intermediate element 200 and the patient interface 100 each are designed as one part and made of plastic, for example a polycarbonate, using injection molding technology. The patient interface is at least to some extent designed as to be elastic and is elastically tensioned during coupling of the second source-sided patient interface coupler 130 with the second patient interface coupler counterpiece 230.

LIST OF REFERENCE SIGNS

100 Patient interface
120 Bore/first source-sided patient interface coupler
130 Spring latch/second source-sided patient interface coupler
131 Spring arm
132 Unlock key
150 Suction ring
151a Outer suction ring wall
151b Inner suction ring wall
152 Gap
153 Patient interface interior
154 Suction ring interior
158 Sucking nozzle
200 Intermediate element
210 Bore/first source-sided intermediate element coupler
220 Pin/first patient-sided intermediate element coupler
230 Counter latch/second patient-sided intermediate element coupler
240 Spring latch/second source-sided intermediate element coupler
240a Catch surface
260 Laser passage window/protective foil
295 Handle
300 Application head for application of optical radiation of a radiation source
310 Pin/first application head coupler
320 Observation window
330 Laser exit window
340 Recess/second application head coupler
340a Interaction surface
340b Catch surface
900 Eye of a patient
905 Cornea

What is claimed is:

1. A patient interface for coupling an ophthalmological application head for application of optical radiation of a radiation source on an eye of a patient, the patient interface comprising:
   a patient-sided interface structure, designed so as to be coupled to the eye of a patient;
   a source-sided interface structure which is designed to rigidly couple the patient interface to the application head or to an intermediate element that is provided to be arranged between application head and patient interface,
   wherein the source-sided interface structure comprises a first source-sided patient interface coupler and an additional second source-sided patient interface coupler,
   wherein the first source-sided patient interface coupler is designed, by establishing a coupling with a first patient interface coupler counterpiece of the application head or the intermediate element, to restrict the mobility of the patient interface relative to the application head or the intermediate element, and
   wherein the second source-sided patient interface coupler is designed, by establishing a coupling with a second patient interface coupler counterpiece of the application head or the intermediate element while the first source-sided patient interface coupler is coupled with the first patient coupler counterpiece, to couple the patient interface rigidly to the application head or the intermediate element.

2. The patient interface according to claim 1, wherein the first source-sided patient interface coupler is designed to interlockingly couple with the first patient interface coupler counterpiece while maintaining at least one degree of freedom.

3. The patient interface according to claim 1, wherein a coupling of the second source-sided patient interface coupler with the second patient interface coupler counterpiece requires that the first source-sided patient interface coupler is coupled with the first patient interface coupler counterpiece.

4. The patient interface according to claim 3, wherein the first source-sided patient interface coupler is designed to create a forced guide for the patient interface with regard to the application head or the intermediate element when coupled with the first patient interface coupler counterpiece.

5. The patient interface according to claim 1, wherein the second source-sided patient interface coupler is designed to couple with the second patient interface coupler counterpiece by means of a snap or latch connection.

6. The patient interface according to claim 1, wherein patient interface is elastic and is elastically tensioned when the second source-sided patient interface coupler is coupled with the second patient interface coupler counterpiece.

7. The patient interface according to claim 1, wherein the coupling of the first source-sided patient interface coupler with the first patient interface coupler counterpiece requires that the second source-sided patient interface coupler is not coupled with the second patient interface coupler counterpiece.

8. The patient interface according to claim 1, wherein the patient interface comprises a grip structure to be held with one hand.

9. The patient interface according to claim 8, wherein the grip structure is integral with the second source-sided patient interface coupler.

10. The patient interface according to claim 1, wherein the patient-sided interface structure comprises a suction ring designed for providing a rigid vacuum coupling with the eye of a patient.

11. The patient interface according to claim 1, wherein the second source-sided patient interface coupler comprises a snap lever which is releasable with one hand.

12. An intermediate element to be arranged between an ophthalmological application head for application of optical radiation of a radiation source and a patient interface, the intermediate element comprising:
   a patient-sided intermediate element interface structure;
   a source-sided intermediate element interface structure,
   wherein the patient-sided intermediate element interface structure comprises a first patient-sided intermediate element coupler and an additional second patient-sided intermediate element coupler,
   wherein the first patient-sided intermediate element coupler forms a first patient interface coupler counterpiece, and the second patient-sided intermediate element coupler forms a second patient interface coupler counterpiece,
   wherein the first patient-sided intermediate element coupler is designed, by establishing a coupling with a first source-sided patient interface coupler of the patient interface, to restrict the mobility of the patient interface relative to the intermediate element, and
   wherein the second patient-sided intermediate element coupler is designed, by establishing a coupling with a second source-sided patient interface coupler of the patient interface while the first patient-sided intermediate element coupler is coupled with the first source-sided interface coupler of the patient interface, to rigidly couple the patient interface to the intermediate element.

13. The intermediate element according to claim 12, wherein the source-sided intermediate element interface structure is designed to rigidly couple the intermediate element to the application head, the source-sided intermediate element interface structure comprises a first source-sided intermediate element coupler and a second source-sided intermediate element coupler, wherein the first source-sided intermediate element coupler is designed to restrict the mobility of the intermediate element relative to the application head when coupled with a first application head coupler of the application head, and the second source-sided intermediate element coupler is designed to rigidly couple the intermediate element to the application head by coupling with a second application head coupler of the application head while the first source-sided intermediate element coupler is coupled with the first application head coupler.

14. An ophthalmological application head for application of optical radiation of a radiation source, comprising:
   a first application head coupler and a second application head coupler, wherein the first application head coupler and the second application head coupler are designed:
   as first patient interface coupler counterpiece for coupling with a first source-sided patient interface coupler of a patient interface to restrict mobility of the patient interface relative to the application head, and as second patient interface coupler counterpiece for coupling with a second source-sided patient interface coupler of the patient interface to rigidly couple the patient interface to the application head while the first patient interface coupler counterpiece is coupled with the first source-sided patient interface coupler; or as first intermediate element coupler counterpiece for coupling with a first source-sided intermediate element coupler of an intermediate element to restrict mobility of the intermediate element relative to the application head, and as second intermediate element coupler counterpiece to rigidly couple the intermediate element to the application head while the first intermediate element coupler counterpiece is coupled with the first source-sided intermediate element coupler.

15. The ophthalmological application head of claim 14, wherein a first patient-sided intermediate coupler of the intermediate element is designed, by establishing a coupling with the first source-sided patient interface coupler of the patient interface, to restrict the mobility of the patient interface relative to the intermediate element, and wherein a second patient-sided intermediate coupler of the intermediate element is designed, by establishing a coupling with the second source-sided patient interface coupler of the patient interface, to rigidly couple the patient interface relative to the intermediate element while the first patient-sided intermediate coupler is coupled to the first source-sided patient interface coupler.

16. The patient interface according to claim 1, wherein the second source-sided patient interface coupler directly contacts the second patient interface coupler counterpiece of the application head or intermediate element when rigidly coupled to the second patient interface coupler counterpiece.

* * * * *